United States Patent [19]

Kissell et al.

[11] 4,010,647
[45] Mar. 8, 1977

[54] SAMPLING METHOD AND APPARATUS
[75] Inventors: Fred N. Kissell; Robert P. Vinson, both of Pittsburgh, Pa.
[73] Assignee: The United States of America as represented by the Secretary of the Interior, Washington, D.C.
[22] Filed: Dec. 24, 1975
[21] Appl. No.: 644,265
[52] U.S. Cl. .............................. 73/421.5 R; 417/94
[51] Int. Cl.² .......................................... G01N 1/22
[58] Field of Search ............. 73/421.5, 424; 417/94
[56] References Cited
UNITED STATES PATENTS

| 1,005,664 | 10/1911 | Snyder | 417/94 |
| 1,134,432 | 4/1915 | Aylsworth | 417/94 |

FOREIGN PATENTS OR APPLICATIONS 468  1911  United Kingdom .......... 73/421.5 R

*Primary Examiner*—S. Clement Swisher
*Attorney, Agent, or Firm*—William S. Brown; Donald R. Fraser

[57] ABSTRACT

A helical open ended tube is rotated so as to pass an open end successively through two different fluid media. Successive slugs, first one and then the other, of the media are captured, screwed along the length of the tube and retained therein for subsequent analysis.

10 Claims, 14 Drawing Figures

SAMPLING METHOD AND APPARATUS

FIELD OF INVENTION

Measuring And Testing, Sampler and Toller, Rotary Separator.

OBJECTS

The primary object of this invention is to provide a fluid sampler for collecting successive samples of one fluid medium, for example, air, interspersed between and separated by slugs of another fluid medium, such as water. To this end it is intended now to provide a helical open-ended tube which is rotated about its helical axis, which is preferably upwardly inclined, so as to dip an open end successively through the atmospheric air and then through water so that slugs of air are collected in the upper portions of the tube convolutions, the air slugs being separated by slugs of water in the lower portions of the convolutions. Either or both of the slugs of fluid media can be analyzed by piercing the appropriate portion of the tube with a hypodermic syringe needle, if the collecting tube be of penetratable material. If the collecting tube be of impenetratable material, the samples may be passed from the collecting tube into another helical tube of penetratable material. This latter arrangement is useful for retaining long-term air samples wherein permeability of a flexible-wall tubing would result in loss of samples because of tube-wall permeability.

A further object is to provide for timing the sample collecting periods. It is preferred, although not necessary, to drive the tube with a spring clock motor, which is a reliable, easily portable device not subject to sparking. Thus the device is safe for use in sampling air in mines where methane gas is a hazard, and it can easily be transported to the surface for analysis. In accordance with one concept, slugs of each of the fluid media, air and water, for example, are derived by swinging an open end of the helical tube slowly through both the air and the water. According to another concept, the open end of the tube is swung slowly through one fluid medium and then rapidly through the other. Thus successive instantaneous samples may be derived. In any case, since the speed at which the helical tube is rotated is regular and known, the times at which the samples were derived can easily be computed.

Still another object is to provide for maintaining the sample slugs separate from one another during transport. To this end it is intended now to provide a method and means wherein one or more elongate clamping members are pinched in against the convolutions of the helical tube so as to seal off the interior of one convolution from the other. Where two clamping members are used, one along each of opposite sides of the helix, two portions of the same convolution can be separated from one another. These concepts relate to the embodiments wherein the wall of the tube is formed of flexible material.

A still further object is to provide for doubling the number of samples taken during a specified time on a given over-all length of helical tubing. According to this concept, it is proposed to provide two coaxial and coextensive helixes, one the inner and the other the outer, wherein their open ends which sweep through the media to be sampled are disposed 180° apart.

It is old to collect a sample liquid or grain by sweeping an open end of a tube through the matter to be sampled, for example, in Morse U.S. Pat. No. 2,327,123 and Bowlier U.S. Pat. No. 3,117,452. The method and means by which a series of fluid samples can be collected and stored separately along the length of a tube constitutes the distinguishing feature of this invention.

These and other objects will be apparent from the following specification, in which.

Figure 8:
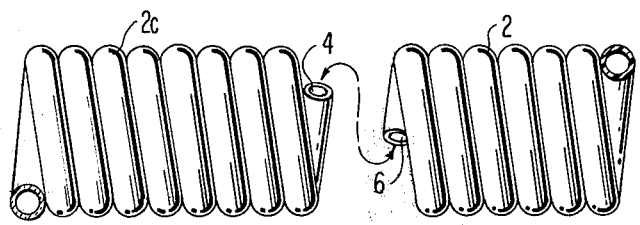
Figure 9:
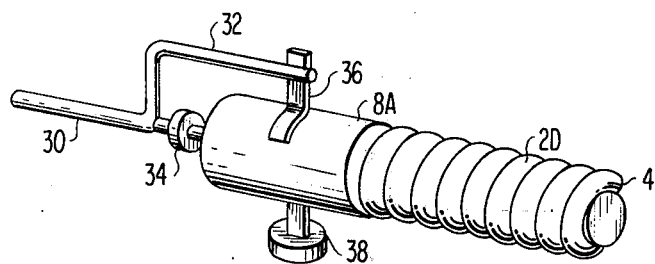
Figure 10A:
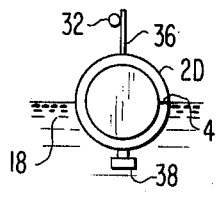
Figures 10B, 10C:
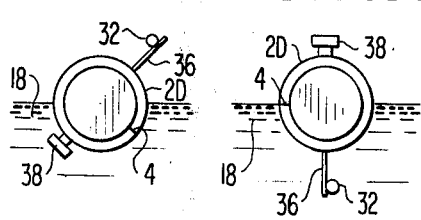
Figure 10D:
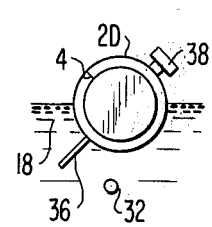
Figure 10E:
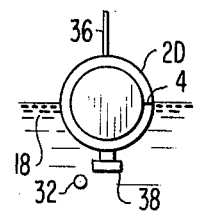

FIG. 8 diagrammatically illustrates the method of transferring samples from an impenetrable helical tube to one that may be penetrated by a hypodermic needle;

FIG. 9 diagrammatically illustrates a drive for obtaining substantially instantaneous samples; and, FIGS. 10a, 10b, 10c, 10d and 10e illustrates the flop-over effect obtained with the drive shown in FIG. 9.

Figure 1:
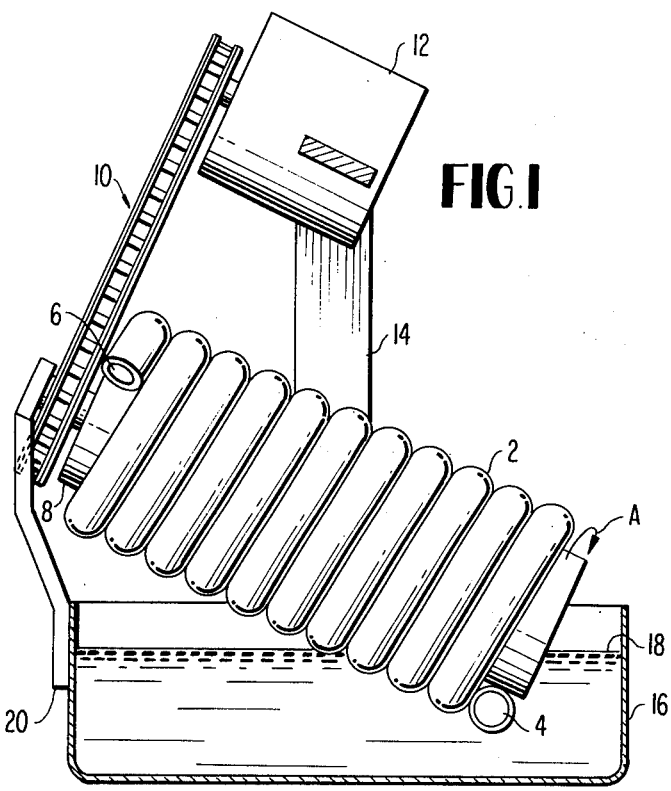
FIG. 1 is a diagrammatic side elevation, partly in vertical cross-section, illustrating the basic method and form of the invention is use for air sampling.

Referring first to FIG. 1 of the drawings, in which like reference numerals denote similar elements, the helical tube 2 having open ends 4 and 6 is supported on the mandrel 8 which is rotated at constant speed by a chain and sprocket drive 10 from a clock motor 12. The motor is supported by a frame diagrammatically illustrated at 14 above a pan 16 having water 18 therein. Mandrel 8 is rotatably supported as by a frame 20 extending upwardly from pan 16 so that the rotational axis of the tube 2 inclines upwardly from the level of the water 18 in the pan. Assuming the tube is rotated in the direction of arrow A, its open end 4 swings successively through the water 18 in pan 16 and then through the air above the water. Each time the open end of the tube swings through the air, a sample slug of air is captured and then, when it swings through the water, a slug of water is captured and these successive slugs of first air and then water are screwed upwardly into the helical tube along its length so that each convolution contains in the upper portion thereof a sample slug of air and in the lower portion a slug of water.

The angle of inclination of the rotational axis of the tube is not critical, but it should be such that the successive slugs of air and water will move upwardly along the length of the tube as the latter is rotated, and that the water will not run out when the tube comes to rest.

While tube 2 is shown as open at both ends, it is sufficient only that the upper end of the tube be vented so as to permit the slugs of water to be pumped in by the rotative action of the tube.

The water slugs, of course, separate the sample slugs of air from one another. When the sampling is completed, the device is transported to a suitable location for testing of the sample slugs.

Figure 2:
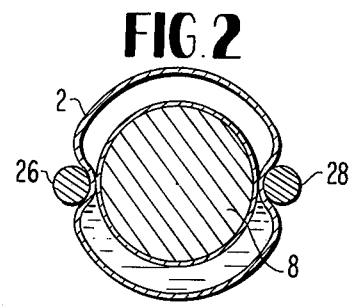
FIGS. 2, 3 and 4 are diagrammatic cross-sections illustrating the application of pinch bars for sealing off portions of tube convolutions so that they will not intermingle during transport.
Figure 3:
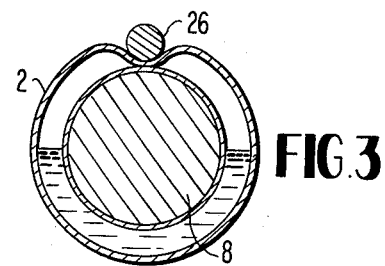
Figure 4:
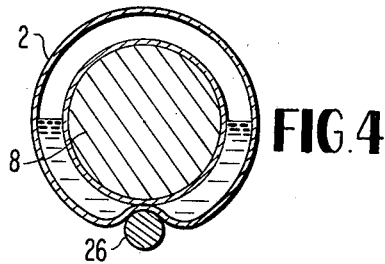

In order to insure against intermingling of the sample slugs, elongate bars 26, 28 may be pressed in against opposite sides of the tube convolutions as shown in FIG. 2 or, alternatively, a single bar 26 may be pressed in against the tops of convolutions as shown in FIG. 3 or against the bottoms of the convolutions as shown in FIG. 4. In the foregoing it has been assumed that tube 2 is formed of a flexible plastic material which is capable of being pinched in as shown in FIGS. 2–4 and which, furthermore, is capable of being penetrated by a hypodermic needle which is stuck in through the tube wall to withdraw sample slugs from the convolutions.

Figure 5:
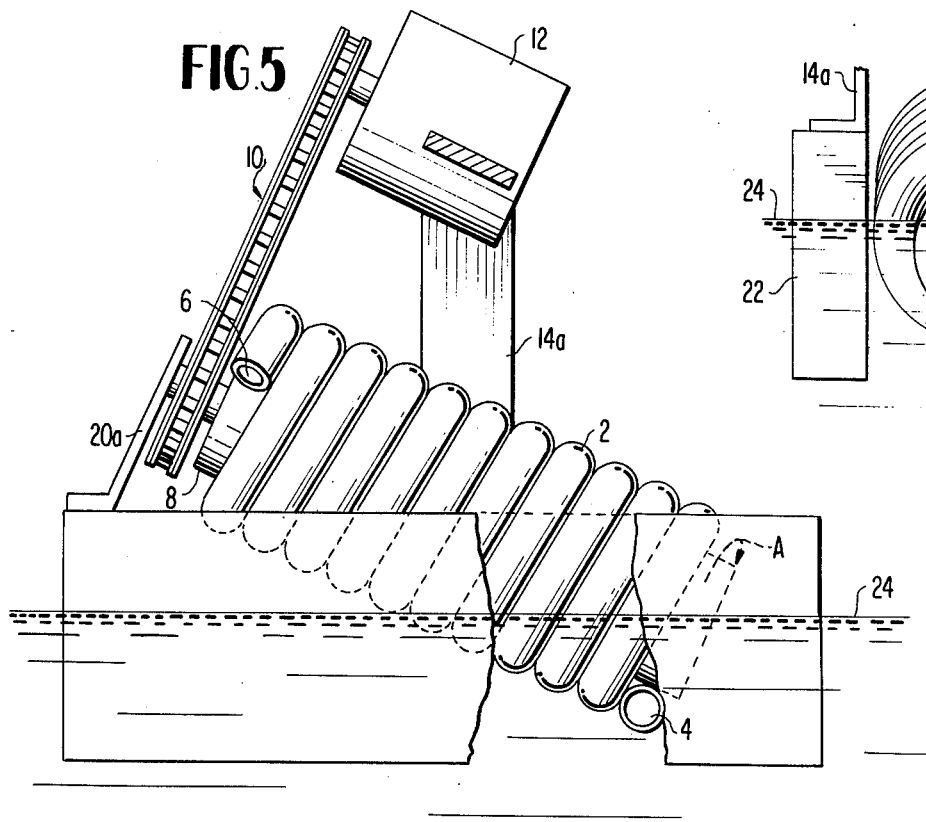
FIG. 5 is a view similar to FIG. 1 but illustrating the invention as used for water sampling.
Figure 6:
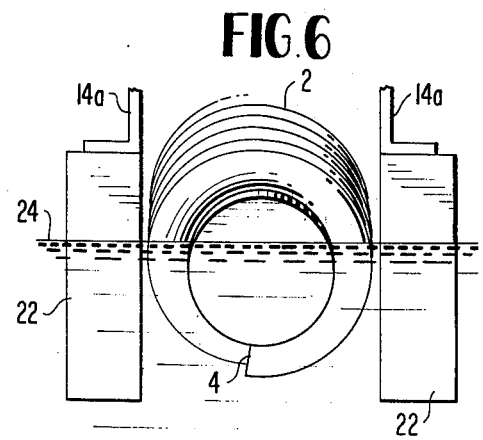
FIG. 6 is a fragmentary end view of the device shown in FIG. 5.

The embodiment illustrated in FIGS. 5 and 6 is substantially like that described above except in this case the device is used for obtaining sample slugs of water. The frame members 14A and 20A are mounted on pontoons 22 which float the apparatus in the water 24 to be sampled.

Figure 7:
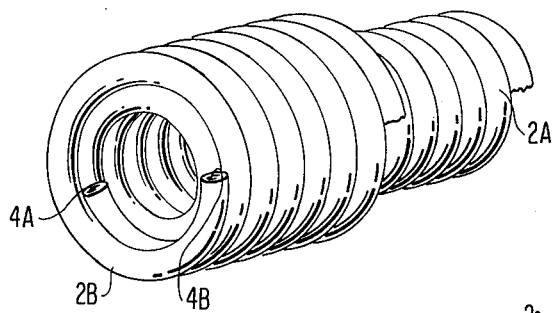
FIG. 7 is a perspective view, partly broken away, showing a double-convolute form of the samples.

FIG. 7 illustrates a modified form of the helical tubing wherein twice as many sample slugs can be obtained without increasing the over-all length of the tube. In this case, inner and outer concentric helical tubes 2A and 2B are arranged with their open ends 4A and 4B disposed 180° apart from one another. These tubes are supported and driven by the means diagrammatically illustrated in FIG. 1 or in FIGS. 5 and 6.

Where samples are to be retained for a long period, it is desirable that they be captured in a helical tube whose walls are impermeable to gas, for example, in a glass tube. However, since the glass tube walls cannot be penetrated by a hypodermic needle, it is desirable that the sample slugs be transferred into a tube whose walls can be penetrated by a hypodermic needle. It is, furthermore, desirable that the slugs, when so transferred, be in precisely the same order as they were when captured. FIG. 8 illustrates the method for accompanying this. The sample slugs are first captured in a helical tube 2c made, for example, of glass. They are transferred in the same order in which they were captured, into a helical tube 2 whose walls are of material which may be penetrated by a hypodermic needle, such as one of the plastics. This is done by connecting the open end 4 of tube 2c to the open end 6 of tube 2 and then the two tubes are rotated together, in the same direction, so as to screw the slugs out of helical tube 2c into the convolutions of helical tube 2.

FIG. 9 illustrates a drive mechanism for capturing substantially instantaneously slug samples of air. In this case the tube 2D has its open end 4 normally disposed at the surface of water 18 so that, when the device is at rest, the open end of the tube is sealed closed by the water. The supporting mandrel 8A for the tube is intermittently driven by a drive shaft 30 which will be presumed to be driven at a regular speed. The drive shaft 30 has a crank arm 32. The mandrel 8A is rotatably supported as, for example, by means of a non-driving connection 34 with drive shaft 30. Projecting outwardly from one side of mandrel 8A is an abutment 36 and on the opposite side of the mandrel is an eccentric weight 38. FIGS. 10a through 10e illustrate the drive cycle. With the device at rest (FIG. 10a) the open end 4 of tube 2D is sealed at the surface of water 18. Crank arm 32 engages abutment 36 and, as it moves clockwise, mandrel 8A is driven clockwise at the same rotational speed as shaft 30. During this phase, a slug of water is captured in the open end 4 of tube 2D. As the assembly rotates, the open end 4 of tube 2D reaches the surface of the water 180° from the starting point. Eccentric weight 38 passes 12 o'clock top center and flops over to its 6 o'clock starting position (FIG. 10e) and in so doing the open end 4 of the tube 2D is swung rapidly through the air until it reaches the surface of the water (FIG. 10e) where it is again sealed until the eccentric arm 32 reaches its FIG. 10a position, whereupon the cycle repeats. The foregoing arrangement is used where substantial instantaneous samples of air are desired. When substantial instantaneous samples of water are desired, either the direction of drive shaft 30 can be reversed or the open end 4 of tube 2D may be disposed 180° from the position shown in FIG. 9.

I claim:

1. The method of obtaining a series of fluid samples which comprises
   rotating a helical tube means about its helical axis while passing an open end thereof successively through first and second fluids of respectively different densities and thereby screwing a plurality of slugs of the first fluid separated from one another by slugs of the second fluid into the tube along the length thereof, and then withdrawing samples by inserting a hypodermic needle through the tube means wall.

2. The method recited in claim 1, wherein two opposite sides of each convolution are pinched together.

3. The method recited in claim 1 including the further steps of passing the successive slugs of the two fluids into another tube means of the same helical configuration as the first-mentioned tube means and having a needle-penetratable wall and then withdrawing samples from said other tube means by inserting a hypodermic needle into the slugs to be sampled through the other tube means wall.

4. The method recited in claim 1 characterized by the fact that the tube means is intermittently rotated so as to pass the open end thereof relatively rapidly through the first fluid and relatively slowly through the second fluid.

5. A sampling apparatus comprising a helical tube means which is open at one end of the helix and vented to the atmosphere at the other end, means for supporting said helical tube means for rotation about an axis which inclines upwardly from said one end of the helix, means for rotating said helical tube means about said axis whereby to swing said open end thereof about an upright circle concentric with the rotative axis of the tube means and in the direction in which the open end of the tube means faces forwardly in the direction of rotation, and means providing for immersion of the open end of the helical tube means in a liquid as the open end of the tube means swings through a lower portion of said circle,
   said means for rotating said helical tube means about said axis including intermittent drive means whereby the open end of said tube means is moved through the lower portion of said circle at one rate and through the upper portion of said circle at a substantially different rate.

6. Sampling apparatus as claimed in claim 5, characterized in that the movement of the open end of the tube through the upper portion of the circle is at a substantially higher rate than through the lower portion of the circle.

7. Sampling apparatus as claimed in claim 5, characterized in that the movement of the open end of the tube through the lower portion of the circle is at a substantially higher rate than through the upper portion of the circle.

8. Sampling apparatus as claimed in claim 5 including means providing for immersion of the open end of the tube in a liquid comprising pontoon means upon which the tube means support means and tube means rotating means are supported.

9. Sampling apparatus as claimed in claim 8, said helical tube means comprising a pair of coaxial helical tubes, one of lesser diameter than the other and disposed within the other, the open end of said helical tubes being disposed 180° apart from one another.

10. The method of obtaining a series of fluid samples which comprises rotating a helical tube means having a wall of flexible material about its helical axis while passing an open end thereof successively through first and second fluids of respectively different densities and thereby screwing a plurality of slugs of the first fluid separated from one another by slugs of the second fluid into the tube along the length thereof, and pinching together the inner sides of the tube means walls on at least one side of each convolution so as to seal off the interior of each convolution from the next adjacent convolution, thereby preventing intermixture of the successive sample slugs.

\* \* \* \* \*